United States Patent [19]

Lim et al.

[11] Patent Number: 5,540,708
[45] Date of Patent: Jul. 30, 1996

[54] POLYMERIC ROTATABLE SHAVER BLADE WITH INTERLOCKING CUTTING TIP

[75] Inventors: Joepert Lim; A. Frank Trott, both of Largo; William F. Mazurek, Palm Harbor; Warren Barrett, Palmetto; W. Lane Ector, Jr., Seminole, all of Fla.

[73] Assignee: Linvatec Corporation, Largo, Fla.

[21] Appl. No.: 326,136

[22] Filed: Oct. 19, 1994

Related U.S. Application Data

[63] Continuation-in-part of Ser. No. 58,504, May 6, 1993, abandoned.

[51] Int. Cl.⁶ .................................................. A61B 17/32
[52] U.S. Cl. ............................... 606/170; 604/22; 30/240
[58] Field of Search .................................... 606/159, 170, 606/171, 180, 167; 604/22; 408/713, 226, 231; 433/144, 145, 146, 147; 30/240, 338; 128/750–755

[56] References Cited

U.S. PATENT DOCUMENTS

| | | |
|---|---|---|
| 4,603,694 | 8/1986 | Wheeler . |
| 4,606,335 | 8/1986 | Wedeen . |
| 4,646,738 | 3/1987 | Trott . |
| 4,735,605 | 4/1988 | Swartz . |
| 4,815,462 | 3/1989 | Clark . |
| 4,883,458 | 11/1989 | Shiber . |
| 4,886,061 | 12/1989 | Fischell et al. . |
| 4,886,490 | 12/1989 | Shiber . |
| 4,979,939 | 12/1990 | Shiber . |
| 5,041,082 | 8/1991 | Shiber . |
| 5,135,481 | 8/1992 | Nemeh . |
| 5,135k531 | 8/1992 | Shiber . |
| 5,152,744 | 10/1992 | Krause et al. . |
| 5,154,724 | 10/1992 | Andrews . |
| 5,269,798 | 12/1993 | Winkler ................................ 606/170 |
| 5,282,821 | 2/1994 | Donahue . |
| 5,320,635 | 6/1994 | Smith . |

FOREIGN PATENT DOCUMENTS

| | | |
|---|---|---|
| 0481760 | 4/1992 | European Pat. Off. . |
| 3828478 | 5/1989 | Germany . |
| 1718792 | 1/1989 | Russian Federation . |

*Primary Examiner*—Gary Jackson
*Assistant Examiner*—William Lewis
*Attorney, Agent, or Firm*—Gene Warzecha

[57] ABSTRACT

A rotatable shaver having inner and/or outer non-metallic elongated blades for use in endoscopic surgical procedures. In one embodiment a rotatable, elongated non-metallic inner tubular member is disclosed for use with a non-rotatable elongated metallic outer tubular member, the inner member having a flexible, non-metallic tubular body, a proximal hub and a distal tip provided with a cutting tip having a cutting edge formed therein. The elongated tubular body of the inner member is mechanically joined at its proximal end to the hub and at its distal end to the cutting tip. The mechanical connection enables the transmission of torque from the proximal end of the inner member to the distal end while sufficiently holding the tip, tube and hub assembly together to enable insertion and removal of the assembly into and from the outer member.

7 Claims, 9 Drawing Sheets

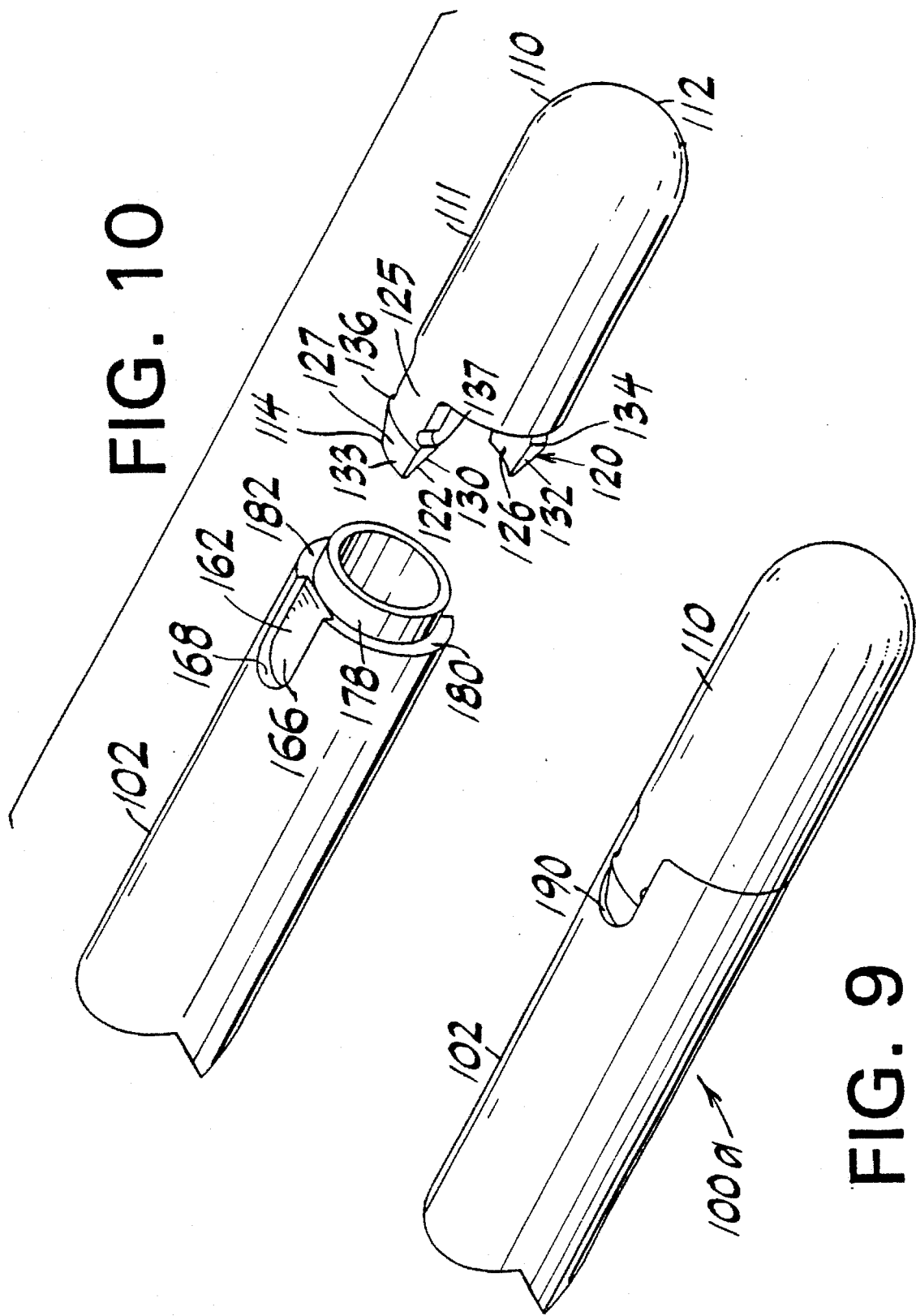

POLYMERIC ROTATABLE SHAVER BLADE WITH INTERLOCKING CUTTING TIP

This application is a continuation-in-part of application Ser. No. 08/058,504, filed May 6, 1993, now abandoned.

BACKGROUND OF THE INVENTION

1. Field of the Invention

The present invention pertains to surgical cutting instruments and, more particularly, to surgical cutting instruments having an elongated inner tubular cutting member rotating about its axis within an elongated outer tubular member having a cutting window at its distal end which cooperates with the inner member to cut, resect or abrade bodily tissue, the resulting loose tissue being aspirated through the lumen of the inner member.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Some conventional surgical cutting instruments (shavers) for use in closed surgery are rotary powered and have a straight, elongated outer tubular member and a straight, elongated inner tubular member concentrically disposed in the outer tubular member. The inner and outer members both separately and jointly are sometimes referred to in the art as "blades". The outer member has a distal end having an opening in the end or side wall (or both) to form a cutting port or window and the inner member has a distal end disposed adjacent the opening in the distal end of the outer member. The inner member is easily insertable into and removable from the outer member to facilitate cleaning or interchanging parts. Each of the elongated members has a hub or termination at its proximal end in order to attach the components to a rotary drive means. The distal end of the inner tubular member has a cutting means or cutting edge for engaging tissue via the opening in the distal end of the outer tubular member. In many cases (but not all) this distal cutting means cooperates with the opening in the outer member to shear, cut or trim tissue. In some cases, such as abrading burrs, the opening in the outer member merely allows access to the tissue and does not otherwise cooperate with the cutting means. The term "cutting edge" or "cutting means" as used herein is intended to include abrading (e.g. burrs) and other devices whether or not there is any traditional cutting or shaving action and whether or not there is any cooperative shearing action. The inner tubular member is rotatably driven about its axis from its proximal end, normally via a handpiece having a small electric motor which is controlled by either finger actuated switches on the handpiece, a foot switch or switches on a console supplying power to the handpiece. The distal end of the inner tubular member can have various configurations depending upon the surgical procedure to be performed, and the opening in the distal end of the outer tubular member would then have a configuration adapted to cooperate with the particular configuration of the distal end on the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as cutting means. The loose tissue resulting from the cutting, resecting or abrading procedure is aspirated through the hollow lumen of the inner tubular member to be collected via a vacuum tube communicating with the handpiece.

The aforementioned elongated surgical cutting instruments have also been produced in angled configurations in which the axes of the distal tips of the inner and outer members are aligned and offset or bent at a fixed angle relative to the axes of the proximal ends of the aligned inner and outer members. Examples of such fixed-angle, rotary surgical instruments are shown in U.S. Pat. No. 4,646,738 (Trott), assigned to the assignee hereof, and in European Patent Application 0 445 918 (Krause et al.). In other respects the operation of these fixed-angle shavers is largely the same as that of the straight shavers described above. Known fixed-angle shavers are generally produced with only one offset angle—usually 15°. Recently a variable-angle rotary shaver system has been introduced (described in a co-pending patent application assigned to the assignee hereof) in which the outer tube may be bent by a user to a user-selected angle while still enabling the inner tube to be selectively inserted into and removed from the outer tube. The angled shavers have a bend with a radius of curvature on the order of two to four inches. Tighter radii would be desirable.

In straight, fixed-angle and variable-angle prior art rotary shavers the inner tubular member has a proximal inner hub shaped to mate within an outer hub situated at the proximal end of the outer tubular member when the two members are assembled. The outer hub serves to lock the outer tubular member to the handpiece while the inner hub is adapted to mate with the motor drive shaft. Since most conventional rotary shavers utilize reusable handpieces with disposable shaver blades, the materials used to make the disposable blades must be cost-effective without adversely affecting performance. Consequently, the inner and outer hubs are generally molded plastic components while the bodies of the inner and outer tubular members are generally made of a biocompatible metal (generally 300 series stainless steel). The latter material is used in prior art inner tubular members because of the necessity to form sharp cutting means at the distal end of the inner member and because of the necessity to transmit a satisfactory amount of torque from the motor to the distal cutting means. The outer tubular member is made from metal in order to adequately hold the rotating inner member and resist any bending or kinking which would prevent rotation of the inner member.

In straight shaver configurations the elongated metallic tubular body of the inner member is generally integrally formed with the cutting means and the proximal end of the body is adhesively, thermally or ultrasonically bonded or otherwise affixed to the plastic hub. In the case of fixed-angle rotary shavers, however, a coupling device is interposed between the body and the cutting means. These prior art angled devices employ an outer member identical to that used in straight configurations (although angled to receive the bendable inner member) while the inner member is made from a metallic tubular body joined to the inner hub, a metallic distal cutting tip and some coupling means to join the two. In the aforementioned European patent application, for example, the coupling means is metallic and integrally formed with the body and tip, the coupling means being merely a portion of the inner member which is provided with relief apertures formed in the cylindrical surface to enable the inner member to bend as it rotates. In this embodiment, the metallic tubular body of the inner member is thermally bonded or otherwise affixed to the plastic hub as in the previously mentioned straight configuration.

Another fixed-angle shaver is known in which the tubular body of the inner member comprises a hollow metallic shaft affixed to the plastic hub, a metallic distal cutting tip and a coupling means formed of a plurality of counter-wound coiled metallic springs bonded to and interposed between the body and the tip. Such an embodiment is disclosed in the aforementioned U.S. Pat. No. 4,646,738 (Trott).

Another fixed-angle shaver is known in which the inner member has a plastic hub bonded to a metallic tubular body, a metallic distal tip and a coupling means formed of a single coil spring covered with a flexible plastic sleeve bonded to and interposed between the body and the tip.

The only known variable-angle shaver system has recently been introduced by Linvatec Corporation, 11311 Concept Boulevard, Largo, Fla. 34643 under the trademark MERLIN. This device incorporates a flexible inner member similar to that disclosed in the aforementioned U.S. Pat. No. 4,646,738 (Trott) and incorporates a unique, user-bendable outer tube.

One disadvantage of known coupling members is their inability to transmit sufficient torque at high rpm's through angles much greater than 15°. As the benefits of angled shavers have been more and more widely appreciated, the angular limitation of prior art angled shavers has become a disadvantage to be overcome. It would, therefore, be advantageous to produce an angled rotary shaver capable of operation at angles greater than 15°.

In each known prior art system the requirement for adequate torque transmission along the inner member from the motor to the distal tip and the requirement for maintaining the sharpness of the cutting edge at the distal tip have been achieved by the use of metallic inner members formed almost entirely from biocompatible metallic materials such as stainless steel. The cost of obtaining and fabricating these materials into inner members is significant even though the combined inner and outer members are intended to be disposable. While the cost is significant even in the straight variety of shaver, the cost increases substantially in the fixed and variable-angle shavers because of the additional complexity involved in these devices. The coupling members of each of the known prior art angled rotary shavers are relatively complex when properly assembled to address the requirements of adequate torque transmission, sufficient lubricity to enable sustained operation at high rpm and sufficient sharpness. The number of component parts (springs, bearing sleeves, tubular bodies, cutting tips, etc.) and their assembly adds to the cost of these devices. It would be advantageous to produce both straight and angled rotatable shaver systems with fewer and/or less costly disposable components.

Another requirement imposed upon rotatable shavers is the necessity to maintain close tolerances between inner and outer members in order to maximize efficiency of operation. Obviously, such close tolerances must be balanced with the need to minimize friction to reduce heat and wear. This is generally done with the use of either lubricants or bearing surfaces—in either case adding to the cost of the device. In the case of angled shaver systems, the necessity to include bearing surfaces is even greater. Additionally, some angled shavers enable the inner member to bend within the outer tube by a configuration which often produces some gaps in the surface of the coupling means of the inner member resulting in a decrease of vacuum through the lumen of the inner member thereby compromising the ability of the device to aspirate tissue shavings through the lumen. This has been overcome in some instances by the use of a flexible polymeric sleeve situated over the bendable, coupling means portion of the inner member thus sealing any gaps while also providing a bearing function. The use of a solid cylindrical polymeric sleeve over a spring in some fixed-angle shavers may obviate the need for an encircling polymeric bearing sleeve. However, such bendable portions have less torque transmitting ability than other versions. The concern about maintaining close tolerances, adequate lubricity and vacuum sealing adds to the cost and complexity of prior art shavers and it would be advantageous to produce an inner member in which the disadvantages associated with these parameters could be minimized.

The rotatable inner members used in known angled shavers are either costlier than comparable straight, unbendable inner members or are not as efficient in transmitting torque. (Some prior art bendable inner members have torque transmission capability which is significantly—up to 50%—less than the straight counterpart.) This is most likely attributable to the coupling member. Nevertheless, this difference makes it necessary for manufacturers of these systems to produce both straight and bendable versions of inner tubular members—creating an undesirable inventory burden. It would, therefore, be advantageous to produce an elongated, rotatable tubular inner member which is less costly than conventional non-bendable inner members and which can be used either in a straight outer tubular member or in an angled outer tubular member without significant loss in its torque transmission ability.

Various embodiments of such elongated, rotatable tubular inner members are disclosed in co-pending application Ser. No. 08/058,504, assigned to the assignee hereof. One particular embodiment which has been found desirable utilizes a tubular member formed of polyetheretherketone (PEEK) which has a conventional plastic hub secured to its proximal end in a unique manner and a conventional metallic cutting tip secured to its distal end in a unique manner. The manufacture of a rotatable inner blade member having such a polymeric tube has been found to be facilitated by the invention disclosed herein and the operation and performance of such blades has been found to be enhanced.

Reliable and repeatable joining of a metallic cutting tip to a polymeric tube, particularly one made of PEEK, is difficult. Given the torsional forces to which the cutting tip is exposed, the junction between the tip and the tube must be preferably reinforced with some mechanical connection between the two elements if adhesive is to be used. However, certain mechanical junctions may weaken the wall of the inner tube so that the joint will fail at low torque values. If the design of the mechanical connection is strong enough, no adhesive or other bonding step is required other than merely pushing the tip onto the tube. Similarly, a mechanical connection may be designed for the proximal end of the tube at its connection to the hub. Such mechanical connections offer a significant advantage over the prior art which requires an adhesive or other bonding step to join the inner tube to the tip and the hub.

It is an object of this invention to produce an elongated rotatable inner tubular member for use in a rotatable shaver, the inner member having a non-metallic tubular body of a biocompatible polymeric or composite material that is mechanically joined to the cutting tip and/or hub of the inner member.

It is also an object of this invention to produce a method of producing a polymeric shaver blade member of a rotatable shaver blade, the method comprising steps for mechanically joining a cylindrical cutting tip to the tubular non-metallic inner member.

It is also an object of this invention to produce an elongated rotatable inner tubular member formed of PEEK that is mechanically joined to a cutting tip and/or hub.

SUMMARY OF THE INVENTION

These and other objects of the invention are achieved by the preferred embodiment described herein which is a rotatable elongated inner shaver blade for use with a non-rotatable outer elongated tubular shaver blade, the inner blade comprising a non-metallic elongated tubular body having a proximal end and a distal end. An engagement means (hub) is mechanically joined to the proximal end of the non-metallic tubular body for attaching the inner blade to a means for rotating it relative to the outer blade, the mechanical junction formed by making the outer surface of the proximal end of the tubular body in a non-circular shape compatible with a similar shape in the hub. A cutting means is mechanically joined to the distal end of the non-metallic tubular body, the mechanical junction formed by longitudinally extending tangs of the cutting tip engaging similarly shaped recesses on the outer surface of the distal end of the tubular body.

BRIEF DESCRIPTION OF THE DRAWINGS

FIG. 9 is a front perspective view of an assembled distal end of an alternate embodiment of a rotatable tubular member.

FIG. 10 is a view of FIG. 9 showing the parts disassembled.

DESCRIPTION OF THE PREFERRED EMBODIMENT

Figure 1:
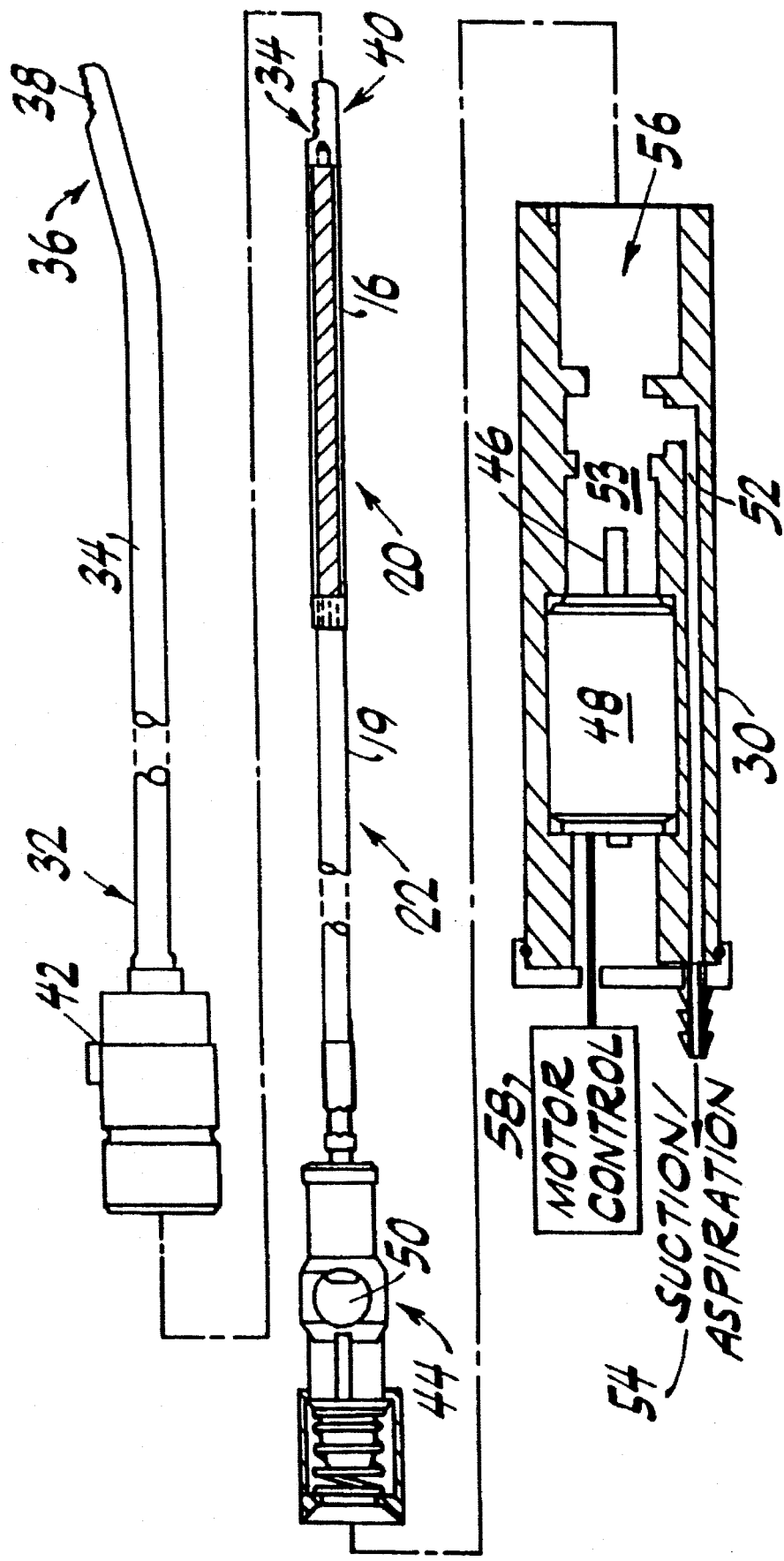
FIG. 1 shows an exploded, partially sectional view of a prior art instrument comprising a handpiece, a torque-transmitting rotatable inner member with a hub, and an outer non-rotatable sheath with a corresponding hub.

As shown in FIG. 1, one example of a prior art angled rotary surgical instrument includes a handle or handpiece 30, a flexible torque-transmitting rotatable inner tubular member 22 and a rigid outer tubular member or sheath 32. While the tubular bodies of the prior art inner and outer tubular members 22 and 32 are metallic, it will be understood below that the present invention discloses non-metallic inner and/or outer tubular members. Inner member 22 has a plastic hub or engagement means 44, a rigid tubular body 19, a flexible coupling section 20 and a distal cutting means 34. The coupling section 20 includes three concentric, coiled springs, as described in the aforementioned Trott patent, encased within a tubular polymeric sleeve 16 as described in U.S. Pat. No. 5,286,253 (Fucci), assigned to the assignee hereof. Outer member 32 has a plastic hub or engagement means 42, a rigid tubular body 34 and a distal window opening 38. As indicated by the dot-dash lines in FIG. 1, the flexible torque-transmitting inner member 22 slides within the outer member 32 such that the rotating cutting means 34 at the distal tip 40 of the inner member is situated adjacent cutting window 38 at the distal tip 36 of the rigid outer member 32.

The instrument is assembled for use by inserting the distal tip of inner member 22 into the proximal end of hub 42 of outer member 32 and sliding hub 42 into recess 56 of handpiece 30 so that hub 44 engages an inner corresponding recess 53 in handpiece 30 and so that motor shaft 46 of motor 48 engages hub 44. At that point the rotatable inner member 22 fits within the interior of stationary outer member 32 with the cutting means 34 exposed at the distal end of the outer member 32. When motor 48 is subsequently actuated by motor control 58, the torque-transmitting inner member rotates, rotating cutting means 34 relative to stationary cutter window 38, thereby forming an effective cutting instrument. Suction or aspiration may then be provided at 54 to withdraw or flush debris from the surgical site. The aspiration is provided via the lumen extending the length of the inner member 22 by way of a port 50 in hub 44 communicating with a passage 52 in the handpiece 30.

In the prior art device, fluid-impermeable sleeve member 16 covers the flexible coupling section 20 to provide a bearing function and allow suction or aspiration applied to the proximal end of the inner member 22 to be effectively communicated to the distal end thereof despite any gaps or slots or openings that may be present in the coupling section. Since the flexible coupling of the inner member comprises a number of substantially circumferential slits formed between the spiral-wrapped wire members, if the distal cutting window becomes clogged or obstructed, the condition known as "blow-by" or unrecoverable loss of suction may occur in the absence of sleeve 16. All known prior art coupling members require attention to this characteristic because of the perforated nature of the coupling.

Figure 2:
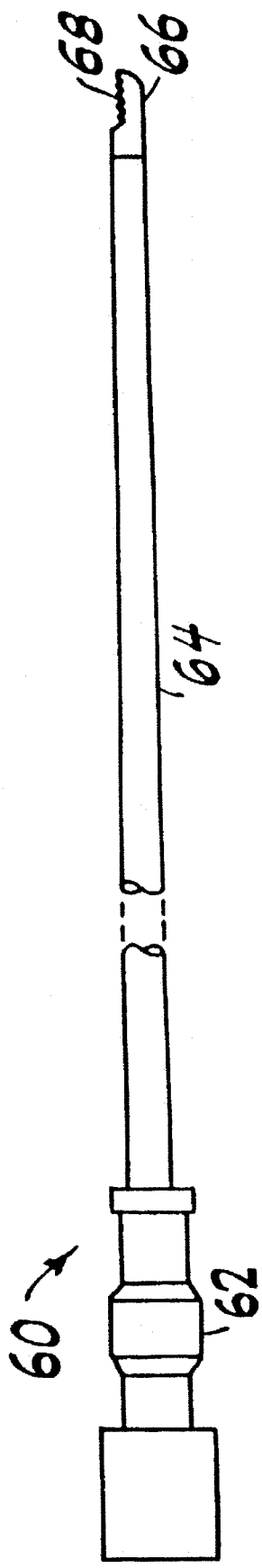
FIG. 2 is a side elevation view of a rotatable inner member constructed in a straight configuration in accordance with the principles of the invention of a co-pending application, assigned to the assignee hereof.
Figure 3:
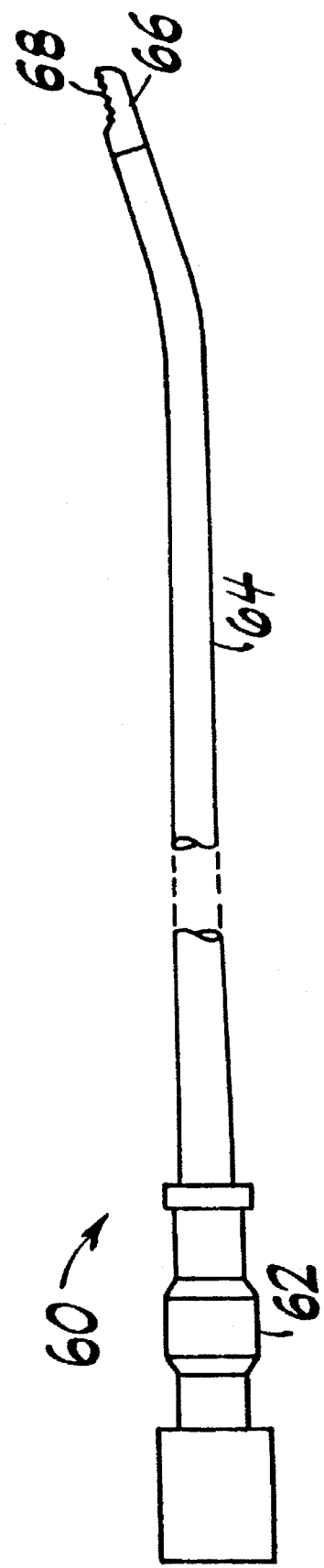
FIG. 3 is a side elevation view of the rotatable inner member of FIG. 2 shown in a curved configuration.
Figure 4:
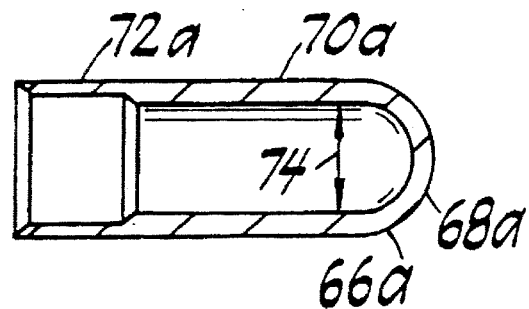
FIGS. 4, 5 and 6 are cross-sectional views of alternate embodiments of a cutting tip or shell which may be attached to the distal end of the non-metallic rotatable inner member shown in FIGS. 2 and 3.
Figure 5:
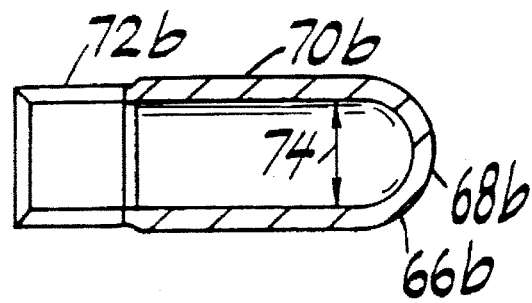
Figure 6:
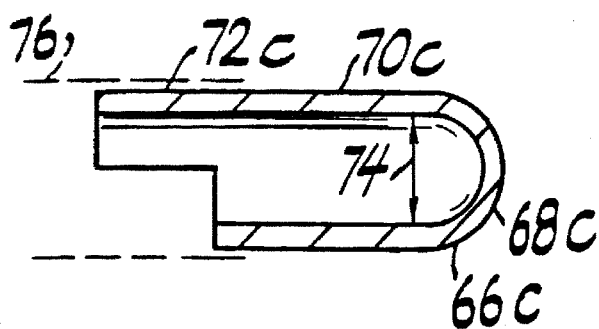

The foregoing description relates to known prior art devices. The invention described in co-pending application Ser. No. 08/058,504, incorporated by reference herein, is an improvement of these known devices and the preferred embodiment of the co-pending application is shown in FIG. 2 comprising a much simplified inner tubular member 60 having a plastic hub 62 at its proximal end, a non-metallic elongated tubular body 64 and a distal metallic cutting means 66 provided with a cutting edge 68. Hub 62 may be a conventional polycarbonate hub used in prior art inner members. Body 64 is a solid-walled, non-perforated tubular body formed of a flexible, non-metallic material that enables member 60 to be rotated about its axis and to transmit torque from the motor via hub 62 to cutting means 66. The rotational speed range may vary from zero to several thousand rpm. Cutting means 66 may be made of a non-metallic material integrally formed with tubular body 64 or may be a separate metallic or non-metallic component. The primary requirements for cutting means 66 are that it be capable of providing a cutting edge 68 (in any one of a variety of shapes such as a plurality of teeth as shown in FIG. 3, a straight edge, etc.) and that it be capable of being securely joined—adhesively or otherwise—to the distal end of tubular body 64 so that sufficient torque may be transmitted through the polymeric inner member to accomplish its intended function. In the preferred embodiment of the co-pending application the cutting means is a separate piece formed of non-galling stainless steel. The piece itself—sometimes referred to as a shell—is conventional and has a rounded front end at the distal end of a cylindrical tubular body and an open rear end at the proximal end of the cylindrical body. Three different embodiments of cutting means 66 are shown in FIGS. 4, 5 and 6 numbered 66a, b and c, respectively. Each cutting means 66a, b and c has a rounded distal tip 68a, b and c, respectively, a cylindrical wall 70a, b and c and a proximal end 72a, b and c. The rounded tips 68a, b and c may be removed in certain applications in the process of forming conventional rotary shaver cutting edges (not shown). Also, any one of a variety of cutting edges may be formed into the wall 70a, b or c. The inner diameter 74 of cutting means should be approximately as big as the lumen of the inner tubular member to be attached to the cutting means. The proximal ends 72a, b and c of the shell are adapted to engage and be joined to the distal end of the inner tubular body. The junction may be formed by making the proximal end of the shell fit around (e.g. 72a) or into (e.g. 72b) the end of the non-metallic tubular inner member as shown in FIGS. 4 and 5, respectively. In either case, one or more of the facing surfaces on the shell and the inner member forming the junction could be knurled or otherwise treated to enhance the strength of the junction. Also, some mechanical interlocking arrangement could be provided as shown in FIG. 6 wherein part of the peripheral wall at the proximal end 72c of the shell is removed to form a rectilinear shape. This proximal end is then adapted to engage a correspondingly shaped distal end (not shown) formed in the inner tubular member. The facing edges of the uniquely shaped junction could then be bonded together. An optional cylindrical sleeve (metallic, polymeric or composite) such as shown in phantom at 76 could overlap both the shell and the tube to enhance the strength of the junction if necessary. The sleeve could be a separate piece or could be injection molded with a metallic cutting shell or integrally formed with a non-metallic cutting shell. Any adhesive or epoxy used to join any of the cutting means and tubular members must obviously be biocompatible.

The variety of possible cutting means 66 is shown to demonstrate that numerous configurations are suitable for use in the invention disclosed in the aforementioned co-pending application. The particular choice depends on the ultimate choice of sizes, materials and torque strengths desired. It has been found that, depending on the choice of materials of the cutting means and tubular body, the connection between them is preferably made by the invention disclosed herein, the preferred embodiment of which is a mechanical interlocking arrangement different from that shown in FIGS. 4, 5 and 6, and best seen in FIGS. 7 and 8. Such an arrangement is advantageous in those situations where a tubular member is made of a material to which metallic pieces do not easily bond via adhesive or other methods. For example, the use of PEEK for the tubular member is desirable for its fatigue resistance, machinability and low coefficient of friction. However, metallic shells cannot easily be adhered to PEEK.

Figure 7:
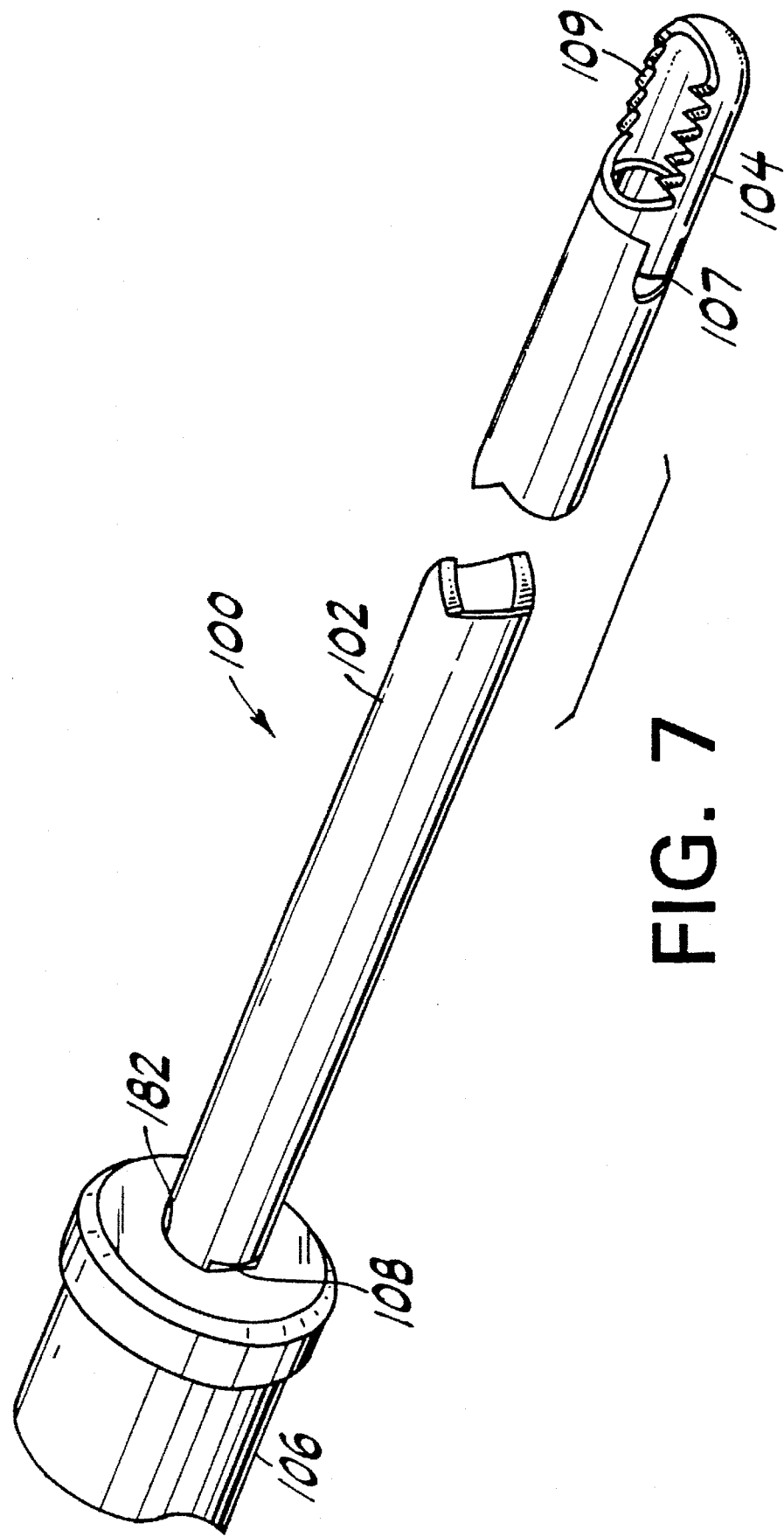
FIG. 7 is a front perspective view of an assembled, rotatable inner member constructed in accordance with the principles of this invention.
Figure 8:
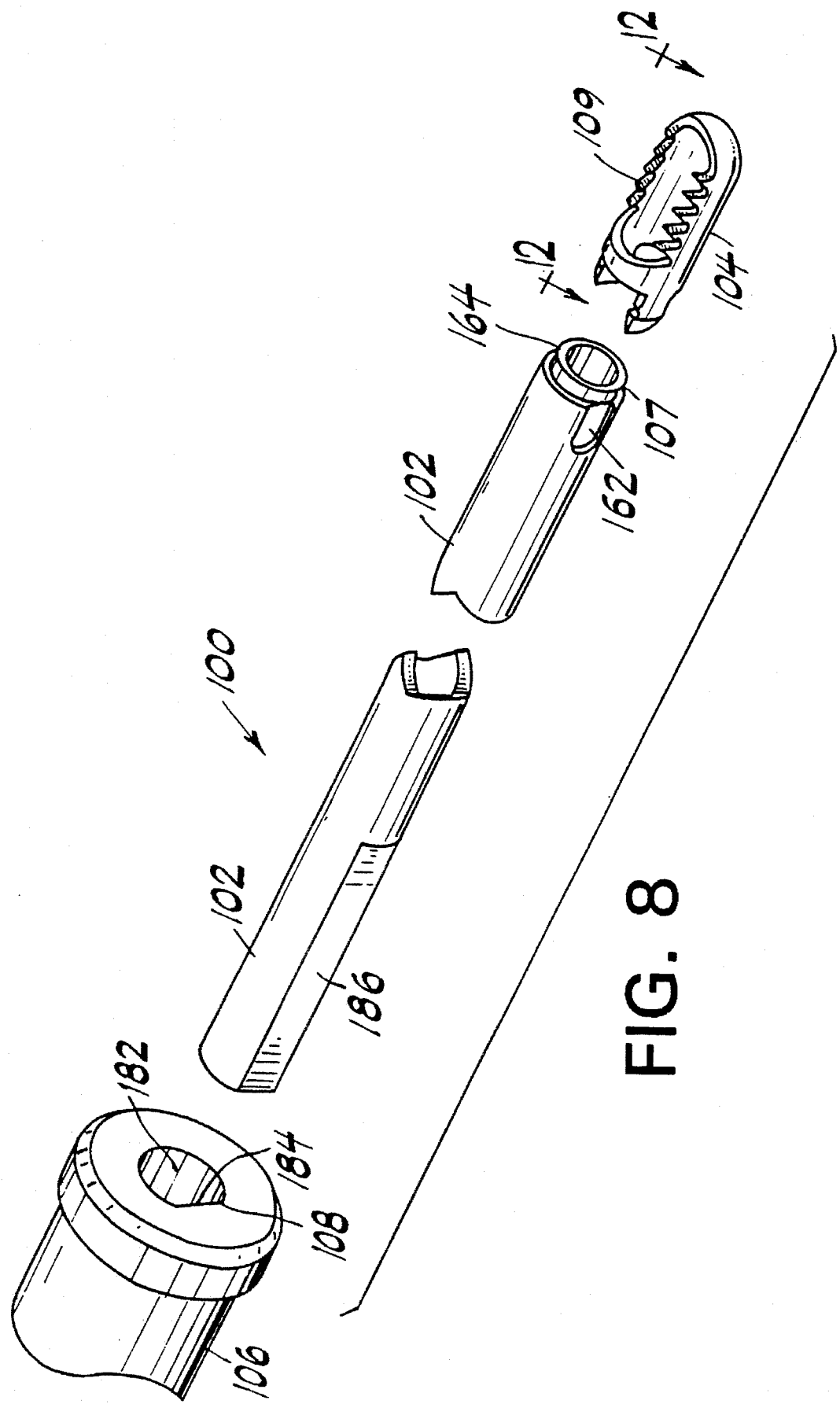
FIG. 8 is a view of FIG. 7 showing the parts disassembled.

As shown in FIGS. 7 and 8, the preferred embodiment of the invention is disclosed herein in the form of inner shaver blade 100 comprising a hollow, polymeric tubular member 102, a cutting tip 104 and a hub 106. As will be understood below, distal junction 107 between tube 102 and tip 104 is solely mechanical and formed without necessitating the use of any adhesive, weld, ultrasonics, etc. Proximal junction 108 between tube 102 and hub 106 is mechanical, supplemented with adhesive.

Cutting tip 104 is exemplary only since the cutting edge 109 may be cut or formed in a variety of conventional patterns from a cutting shell 110, best seen in FIG. 9. FIG. 9 shows the distal end of a shaver blade 100a identical in all respects to shaver blade 100 except that tube 102 is connected to a cutting shell 110 into which a cutting edge (or window in the case of an outer shaver blade) has not yet been formed. It will be understood that the following description pertains equally to shell 110 and tip 104 (and the terms may be used interchangeably), the only difference being that the latter has a cutting edge and the former is shown at a stage of manufacture where it does not yet have an edge (or window). It will also be understood that while shell 110 is shown assembled with tube 102, this is done for the sake of clarity, to simplify the drawings, and in practice some cutting edges would normally be produced in shell 110 prior to its assembly with tube 102.

Figure 11:
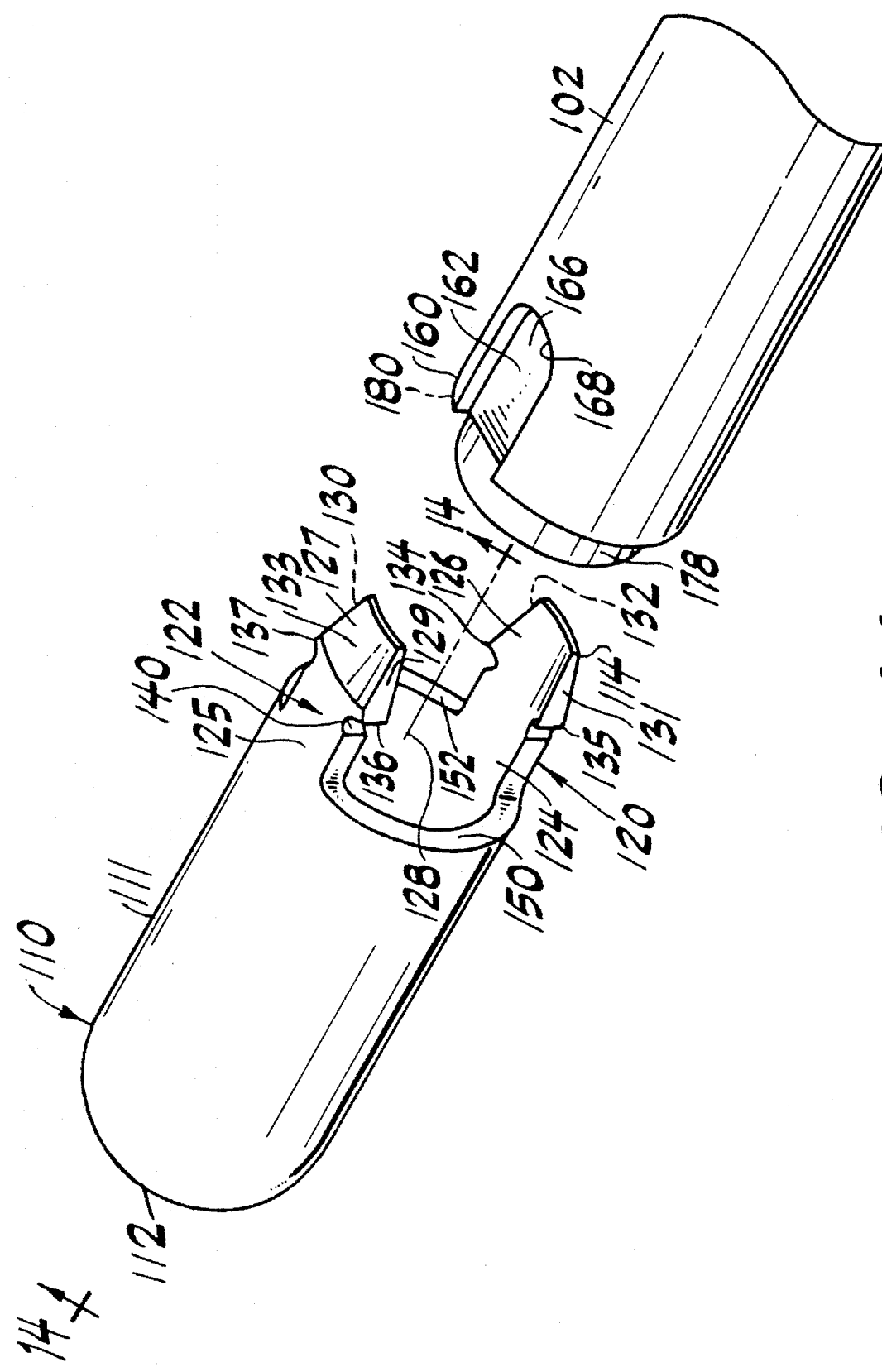
FIG. 11 is a rear perspective view of FIG. 10.
Figure 12:
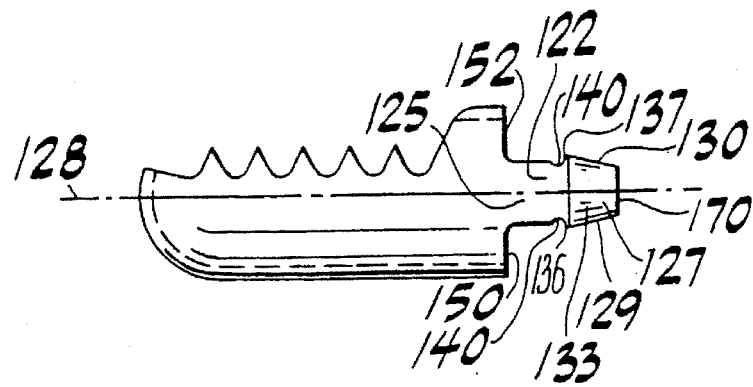
FIG. 12 is a side elevation view of the cutting tip of the rotatable inner member of FIG. 7 taken along the line 12—12.

Cutting shell 110, best seen in FIGS. 9–11 comprises a cylindrical wall 111, a closed distal end 112 and an open proximal end 114. While distal end 112 is shown closed, it will be understood that other embodiments of the invention may require an open distal end. Proximal end 114 is provided with two, diametrically opposed tangs or projections 120 and 122 aligned with wall 111 and extending longitudinally therefrom in a proximal direction (i.e. toward hub 106). While cutting shell 110 may be initially manufactured with proximal end 114 shaped as shown, it has been found that a conventional cutting shell, already used to make certain bendable and non-bendable, metallic body tubular inner members, may be cut to the shape shown herein. Each projection 120 and 122 has a first, rectangular body portion 124 and 125, respectively, and a second, frustoconical tip portion 126 and 127, respectively. Each tip portion 126 and 127 has symmetrical side surfaces 129, 130 and 131, 132, respectively, aligned in two intersecting, transversely extending planes oblique to the longitudinal axis 128 (best seen in FIGS. 12 and 13). Each tip portion 126 and 127 is also tapered on its radially outer surface 133 in a longitudinal direction (best seen in FIGS. 13 and 14). The distal end of frustoconical tip 126 forms transversely extending locking barbs 134 and 135. Similarly, frustoconical tip 127 has locking barbs 136 and 137. Adjacent each barb on its distal side is a semi-circular cutout 140 formed in the proximal end of each side of tang body portions 124 and 125. These cutouts are the result of the manufacturing process used to achieve sharpness on the barbs and a different manufacturing process may result in a cutting tip without these features. The proximal end of shell 110 terminates in arcuate, proximally facing end surfaces 150 and 152 which join the bases of tangs 120 and 122. The proximal ends 170, 171 of tangs 120, 122 are straight and perpendicular to the shell axis because of the original shape of shell 110, however, other shapes of ends 170, 171 may be suitable.

Figure 14:
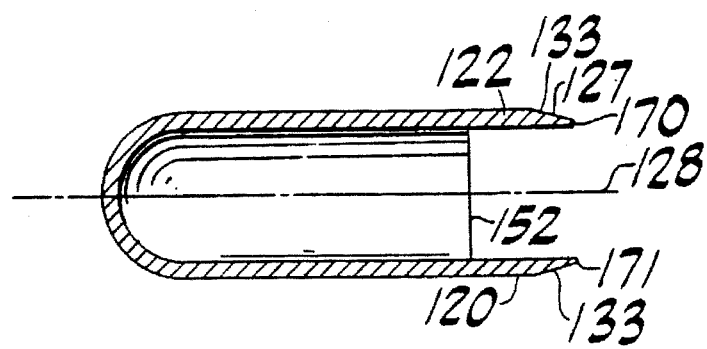
FIG. 14 is a side elevation view of the cutting shell shown in FIG. 11 taken along the lines 14—14.

The distal end 160 of tubular member 102 is formed in a somewhat complementary manner to receive the proximal end of cutting shell 110 in a mechanical, interlocking engagement. End 160 is provided on its outer surface with a pair of diametrically opposed, longitudinally extending recesses 162 and 164 for receiving tangs 120 and 122, respectively. These recesses may be milled into the outer surface of tube 102 and, in the preferred embodiment, each recess 162 and 164 has a flat floor surface 166 and 167, respectively. While the recesses need to be generally rectangular to conform to the rectangular shape of tangs 120 and 122, the particular tool used to form the recesses may incidentally produce rounded back edges 168 and 169, respectively. The radial depth of recesses 162 and 164 is less than the wall thickness of tube 102 and is substantially the same as the thickness of tangs 120 and 122 in order to smooth the transition between the outer diameter of the tip and the tubular member. The thickness of the tangs is, in turn, equal to that of wall 111 as best seen in FIG. 14. A centering shoulder 178 is formed at end 160 with an outer diameter substantially equal to the inner diameter of cutting tip 104. End wall sections 180 and 182 are provided adjacent to shoulder 178.

The length of tangs 120, 122 is approximately equal to the length of recesses 162, 164 to minimize the amount of material removed from the surface of the tubular member. The width of the tangs is chosen to be equal to or less than that of the recesses along most of the length of the tangs except in the area of the barbs so, as will be understood below, the barbs can become embedded to create a locking fit.

Figure 15:
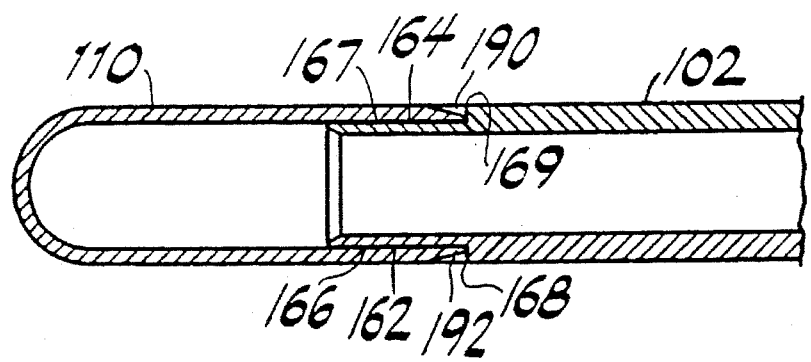
FIG. 15 is a side elevation view in cross-section of FIG. 9.

When assembled, cutting shell 110 (or tip 104) and tubular member 102 need merely be pushed together, with no adhesive necessary, to engage tangs 120 and 122 with recesses 162 and 164, respectively, as best seen in FIGS. 7, 9 and 15. As the pieces are assembled, the barbs on the tangs will temporarily push the side walls of their respective recesses outwardly as the cutting tip is advanced to permit the tangs to be received in the recesses. When fully seated as shown in FIGS. 7, 9 and 15, the tip end walls 150 and 152 will abut the tubular member end walls 180 and 182, respectively, and the metallic barbs will be embedded into the relatively soft side walls of the recesses.

Figure 13:
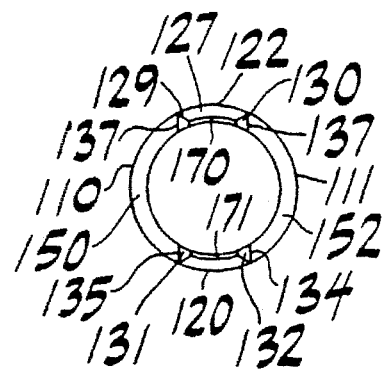
FIG. 13 is an end view, facing distally, of the cutting shell shown in FIG. 11.

The connection between tube 102 and shell 110 is further enhanced by the shapes of the mating structures. For example, tangs 120 and 122 have an arcuate cross-section in a plane perpendicular to the shell axis, as best seen in FIG. 13, while the floor of each recess 162 and 164 is flat. The resulting interference as the tangs are seated enhances the strength of the junction. The taper of frustoconical tip portions 126 and 127 results in small spaces 190 and 192 above the proximal ends of the tip portions to accommodate any material flow and minimize any increase in the outer diameter of the shaver blade at the juncture of the tangs with the recesses. Depending upon materials and processes utilized to make the assembly, the tip portions 126, 127 may not need to be tapered.

While the dimensions of a particular cutting tip/tubular member vary depending on the desired size of the final product, the relative dimensions used in the preferred embodiment have been found acceptable in enhancing performance of blade 100 with respect to torque transmission and pull-out strength. For example, an embodiment utilizing a PEEK inner tube having a 0.140 inch O.D. and a 0.090 inch I.D. would mate with a cutting tip 104 (or shell 110) having 0.140 inch O.D. and 0.120 inch I.D. The inner tube recesses 162 and 164 could then have a width of 0.050 inches and a length of 0.100 inches to mate with tang body portions 124, 125 which are 0.040 inches wide and 0.050 inches long, and tip portions 126, 127 which are 0.045 inches long (from the barbs proximally). The tang width at the barbs is, at 0.062 inches, wider than the recesses to enable a secure connection. Tube shoulder 166 could have an O.D. of 0.110 inches and length of 0.030 inches. Any significant departure from these approximate relative dimensions could result in unacceptably decreasing torsional and/or pull-out strength. For example, if the tangs are not wide enough they may bend under load and if they are too wide, the strength of the inner tube adjacent the recesses may be compromised.

Figure 16:
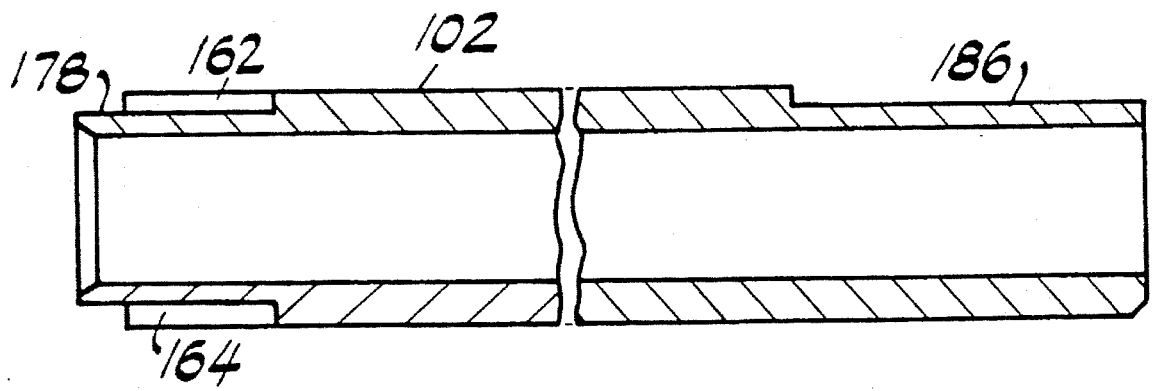
FIG. 16 is a cross-sectional view of the tubular member of FIG. 8.

Turning now to the proximal end of the assembly, as best seen in FIGS. 7, 8 and 16, hub 106 has an axial throughbore 182 with a flat portion 184 on one side (another, non-circular cross-section could also be utilized instead). The proximal end of tube 102 has a D-shaped cross-section produced by a flat portion 186 which is complementary to flat portion 184. An arbitrary convention is established herein by numbering recess 162 as being the one formed parallel to flat portion 186. When hub 106 and tube 102 are pushed together, frictional engagement provides torsional and pull-out strength. Some adhesive may be used to further enhance pull-out strength.

While the preferred embodiment disclosed herein relates to the inner blade of a rotatable shaver, it will be understood that the invention is equally applicable to an outer blade. The cutting shell attached to the aforementioned tubular member can be used to provide a cutting window if the invention is provided in the form of an outer blade. Also, while an even number and symmetrical arrangement of tangs is shown, other variations may be possible.

It will be understood by those skilled in the art that numerous modifications and improvements may be made to the preferred embodiment of the invention disclosed herein without departing from the spirit and scope thereof.

What is claimed is:

1. An elongated blade for a rotatable shaver comprising:

a hollow, cylindrical, cutting tip having a cylindrical wall, a distal end and a proximal end, said tip provided with a cutting edge therein;

at least one longitudinally extending projection extending proximally from said proximal end of said tip, said projection subtending an arcuate distance less than 360°; and a hollow, cylindrical, polymeric tubular member having a proximal end, a distal end and a predetermined wall thickness with an outer surface thereon, said distal end of said tubular member having formed therein at least one longitudinally extending recess in said outer surface of said tubular member, said recess adapted to receive said projection and having a predetermined radial depth which is less than said predetermined wall thickness, said recess subtending an arcuate distance less than 360°.

2. An elongated blade according to claim 1 further comprising:

a pair of diametrically opposed, longitudinally extending projections extending proximally from said proximal end of said tip; and said distal end of said tubular member having formed therein a pair of generally rectangular diametrically opposed, longitudinally extending recesses in said outer surface of said tubular member, said recesses adapted to receive said projections and having a predetermined radial depth which is less than said predetermined wall thickness.

3. An elongated blade according to claim 2 wherein each of said projections further comprises:
- a first portion aligned with said cylindrical wall and extending proximally from the proximal end thereof, said first portion having a proximal end and a distal end and a predetermined transverse width; and
- a second portion aligned with said cylindrical wall and extending proximally from the proximal end of said first portion, said second portion having a proximal end and a distal end and having a frustoconical shape transversely wider at its distal end than at its proximal end.

4. An elongated blade according to claim 3 wherein said first and second portions are transversely arcuate in cross-section.

5. An elongated blade according to claim 2 wherein each of said projections further comprises:
- at least one arcuately extending lateral projection for being embedded in the surface of the distal end of said tubular member adjacent a corresponding one of said recesses.

6. A method of producing a polymeric shaver blade member of a rotatable shaver blade comprising the steps of:
- providing a cylindrical cutting tip having a pair of diametrically opposed, longitudinally extending projections extending proximally from said proximal end of said tip; and
- providing a hollow, cylindrical polymeric tubular member having a proximal end, a distal end and a predetermined wall thickness, said distal end of said tubular member having formed therein a pair of generally rectangular diametrically opposed, longitudinally extending recesses in the outer surface of said tubular member, said recesses adapted to receive said projections and having a predetermined radial depth which is less than said predetermined wall thickness;
- aligning said projections with said recesses; and
- pushing said cutting tip and said tubular member together.

7. A method according to claim 6 further comprising the step of forming in said tubular member a cylindrical centering shoulder, axially aligned at the distal end thereof, prior to pushing said cutting tip and said tubular member together.

* * * * *